United States Patent [19]

Appleton

[11] Patent Number: 4,830,960

[45] Date of Patent: May 16, 1989

[54] DETERMINATION OF CHLAMYDIA TRACHOMATIS

[75] Inventor: Peter N. Appleton, Cambridge, United Kingdom

[73] Assignee: IQ (Bio) Limited, Cambridge, England

[21] Appl. No.: 791,131

[22] Filed: Oct. 24, 1985

[30] Foreign Application Priority Data

Oct. 25, 1984 [GB] United Kingdom ................. 8427006

[51] Int. Cl.[4] .................... G01N 33/53; G01N 33/543; C12Q 1/42
[52] U.S. Cl. .......................................... 435/7; 435/21; 435/25; 435/26; 435/29; 436/518; 436/825
[58] Field of Search ................... 435/7, 21, 29, 25, 26, 435/183; 436/147, 811, 825, 518

[56] References Cited

U.S. PATENT DOCUMENTS

| | | | |
|---|---|---|---|
| 4,272,504 | 6/1981 | Kim et al. | 436/825 |
| 4,299,815 | 11/1981 | Hansen et al. | 436/825 |
| 4,361,647 | 11/1982 | Remington et al. | 435/7 |
| 4,446,231 | 5/1984 | Self | 435/26 |
| 4,474,878 | 10/1984 | Halbert et al. | 435/26 |
| 4,497,899 | 2/1985 | Armstrong et al. | 436/811 |
| 4,598,042 | 7/1986 | Self | 435/26 |
| 4,617,264 | 10/1986 | Whiteley et al. | 435/34 |
| 4,652,518 | 3/1987 | Makela et al. | 436/811 |
| 4,663,291 | 5/1987 | Rose | 435/259 |
| 4,683,196 | 7/1987 | McLaughlin | 435/7 |

OTHER PUBLICATIONS

Caldwell et al; Infection and Immunity, May 1984, pp. 306–314, vol. 44, No. 2; Monoclonal Antibody Against a Genus-Specific Antigen of Chlamydia Species: Location of the Epitope on Chlamydial Lipopolysaccharide. Brade et al; Proc. Nat'l. Acad, Sci. USA 84 (1987) pp. 2508–2512; Chemical and Serological Investigations on the Genus-Specific Limopolysaccharide Epitope of Chlamydia.

Thornley et al; Journal of General Microbiology (1985) 131, pp. 7–15 Properties of Monoclonal Antibodies to the Genus-Specific Antigen of Chlamydia and their use of Antigen Detection by Reverse Passive Haemagglutination.

Primary Examiner—Robert J. Warden
Assistant Examiner—Janelle Graeter
Attorney, Agent, or Firm—Cushman, Darby & Cushman

[57] ABSTRACT

A process for determining qualitatively or quantitatively the presence of *Chlamydia Trachomatis* or *Chlamydia trachomatis* derived material in a subject material which process comprises deriving a sample from said subject material *Chlamydia trachomatis* derived material, contacting said sample with an antibody for a *Chlamydia trachomatis* derived material bound to a substrate thereby to bind at least a portion of the *Chlamydia trachomatis* derived material, contacting the bound *Chlamydia trachomatis* derived material with a conjugate between a substance which will bind selectively to the *Chlamydia trachomatis* derived material and a catalyst for a reaction system thereby to bind said conjugate to said bound *Chlamydia trachomatis* derived material, carrying out the reaction system catalysed by said catalyst and determining a product of said reaction system, characterised in that the sample is derived from the subject material by a process including heating the subject material to an elevated temperature and for a period of time such as to enhance the determination.

10 Claims, No Drawings

DETERMINATION OF CHLAMYDIA TRACHOMATIS

The present invention relates to the determination qualitatively or quantitatively of the presence of *Chlamydia trachomatis* in materials.

A known procedure for conducting determinations of *Chlamydia trachomatis* and also having wider applicability is the use of an immunoassay system such as ELISA. Generally, in such an immunoassay a sample containing or suspected to contain *Chlamydia trachomatis* derived material, particularly a *Chlamydia trachomatis* antigen is contacted with a support such as a microplate which will bind *Chlamydia trachomatis* material. The plate is then washed leaving *Chlamydia trachomatis* material bound to the support. The bound *Chlamydia trachomatis* material is then contacted with a conjugate between an antibody which will bind to the *Chlamydia trachomatis* material and a substance which will catalyse a detectable reaction system either directly or through an intermediate process. This process produces a concentration of bound catalyst related to the concentration of *Chlamydia trachomatis* material in the original sample. The bound enzyme is used to catalyse a reaction which may be detectable either visually or by a machine.

In a modification of this procedure, the bound catalyst is an enzyme which is used to catalyse a reaction which produces a trigger for a further reaction or set of reactions. Such systems are known as amplified enzyme immunoassay systems.

The assay depends upon the specific binding of the catalyst enzyme to the bound antigen. Any binding of catalyst enzyme to the support which is not through binding to the antigen is termed "non-specific binding" and will produce bound enzyme which will catalyse the detecting reaction producing a signal which is not related to the concentration of the antigen in the sample.

It is known that all members of the genus Chlamydia share a common group antigen characterised by its resistance to heating (Schacter, J. and H. D. Caldwell 1980. Chlamydiae. Annu. Rev. Microbiol. 34: 285–309). Furthermore lipopolysaccharide (a common group antigen) has been extracted by hot phenol-water (Westphal, O. and K. Jann. 1965. Bacterial lipopolysaccharides. Extraction with phenol water and further applications of the procedure. Methods. Carbohydr. Chem. 5: 84–91).

Surprisingly however, it has now been found that non-specific binding can be decreased and that specific binding can apparently be increased by heating the *Chlamydia trachomatis* antigen containing material under test, such as swabs, prior to conducting the enzyme linked immunoassay.

Accordingly, the present invention provides a process for determining qualitatively or quantitatively the presence of *Chlamydia trachomatis* or *Chlamydia trachomatis* derived material in a subject material which process comprises deriving a sample from said subject material containing *Chlamydia trachomatis* derived material, contacting said sample with an antibody against a *Chlamydia trachomatis* derived material bound to a substrate thereby to bind at least a portion of the *Chlamydia trachomatis* derived material, contacting the bound *Chlamydia trachomatis* derived material with a conjugate between a substance which will bind selectively to the *Chlamydia trachomatis* derived material and a catalyst for a reaction system thereby to bind said conjugate to said bound *Chlamydia trachomatis* derived material, carrying out the reaction system catalysed by said catalyst and determining a product of said reaction system, wherein the sample is derived from the subject material by a process including heating the subject material to an elevated temperature and for a period of time such as to enhance the determination.

Preferably, the material is heated to a temperature from 70° to 110° C.

Preferably the material is heated to a temperature of from 80° to 100° C.

Generally, an improvement in the determination will be obtained by maintaining the material at the elevated temperature for longer than five minutes. Preferably, the material is maintained at the elevated temperature from 5 to 40 minutes. It is generally found that no further improvement in the determination is obtained by holding times longer than this and there may be some gradual deterioration in the determination from the optimum upon long holding times.

Generally speaking, it is preferable to heat for the shortest time likely to enhance the determination to the maximum amount possible by this method.

Generally, such optimum enhancement will be obtained by heating from 5 to 30 minutes, generally approximately 15 minutes.

The material heated may be swabs such as cervical or urethral swabs. Preferably, swabs free from wood, e.g. having a plastics stick, are used.

The heating may however be carried out on the sample immediately ready for analysis e.g. an extract of a sample swab. Alternatively, the sample may be subjected to other procedures to ready it for analysis following the heating stage.

This heating procedure may be employed in any immunoassay technique for the determination of *Chlamydia trachomatis* or more generally in analysis systems as described above.

Preferably however, the analysis system is an enzyme linked system so that the reaction system catalyst referred to above is an enzyme.

Preferably, the conjugated enzyme is a phosphatase, either an acid-phosphatase or an alkaline phosphatase being acceptable.

Preferably, the assay is for a lipo-polysaccharide antigen of *Chlamydia trachomatis*.

Preferably the reaction system is such as to provide an assay of the amplified type so that the reaction system catalyst catalyses a first reaction which produces a modulator for a secondary part of the reaction system.

Suitable assay systems are disclosed in European Patent applications Nos. 84304328, 0027036 and 0060123 and in specification No. 0058539 and are otherwise well known.

As disclosed in those specifications, the modulator produced by the first reaction is preferably NAD which is obtained by the conversion by a conjugated phosphatase (as the reaction system catalyst) of NADP to NAD.

The NAD produced can then act as a modulator for a reduction/oxidation reaction through undergoing an NAD/NADH cycle.

In connection with such preferred analysis systems, it has been found that the presence of certain types of detergent is undesirable during the sample heating stage. Small amounts of certain detergent are desirably present during certain enzyme linked immunoassays to reduce non-specific binding. However, it appears that the presence of certain types of detergent during the heating stage interferes with the subsequent analysis.

Accordingly, if detergent is present during heating, it should be selected to be compatible with this procedure. An example of a suitable detergent is Triton X-705. Zwitterionic detergents should generally be avoided.

It has been found that the presence at the heating stage of divalent cations, specifically magnesium and zinc ions, is beneficial. Magnesium and zinc are usually included in solutions used for the storage or use of enzymes as they prevent degradation of the enzyme on keeping. This does not explain the benefit obtained in the present invention from their presence as no enzyme connected with the assay is normally present at this stage in the solution being heated.

Accordingly, it is preferred that there is present during the heating stage a divalent cation, preferably zinc and/or magnesium. Preferably, both are present. Suitable concentrations are up to 5 mM $Mg^{2+}$ and up to 0.5 mM $Zn^{2+}$. Concentrations as low as 0.5 mM $Mg^{2+}$ and 0.05 mM $Zn^{2+}$ have been found beneficial. Best results have been obtained using a combination of 2 mM $Mg^{2+}$ and 0.2 mM $Zn^{2+}$. These ions may suitable be present as chlorides. Other compatible salts may be used.

It has also been found that the presence of protein material during the heating stage is beneficial. The protein should be chosen such that it will not coagulate at the concentrations used. Partially hydrolysed gelatins have been found suitable as well as foetal calf serum. Suitable gelatin derived proteins are available under the Trade Mark BYCO. Byco A is preferred. This is produced by enzymic hydrolysis of gelatin to produce a cold water soluble protein of number average molecular weight of 2,500 to 4,000 (Formol titration method) or 11,000 (gel permeation chromatography).

Suitable concentrations for use in the heating stage of the present process are from 0.5 to 5% w/v. Preferably from 1 to 2% w/v is used.

Accordingly, the invention includes a heating medium for use in a method as described above comprising assay enhancing concentrations of a divalent cation and a soluble protein.

Preferably, the divalent cation concentration is from 0.05 to 5 mM, and the protein concentration is from 0.5 to 5% w/v.

More preferably, the solution contains $Mg^{2+}$ at from 0.5 to 5 mM (e.g. 1 to 2 mM) and/or $Zn^{2+}$ at from 0.05 to 0.5 mM (e.g. 0.1 to 0.2 mM).

Preferably, the medium contains the protein at from 1 to 2% w/v.

The invention includes an assay kit comprising such a heating medium.

The invention will be illustrated by the following examples:

EXAMPLE 1

Known culture negative and known culture positive specimens (cervical swabs in transport medium) were tested for the presence of Chlamydia trachomatis by an amplified enzyme linked immunoassay. Measured amounts (200 μl) of samples of solution derived from the swabs were incubated at 18° to 22° C. in wells of an antibody coated microtitre plate for 60 minutes. After incubation 50 μl of a conjugate of an alkaline phosphatase with a murine monoclonal antibody reactive with Chlamydia trachomatis was added to each well and the plate was incubated for a further 60 minutes. The plate was throughly washed and the amount of bound phosphatase, and hence the Chlamydia trachomatis concentration of the sample, was measured by adding measured amounts of substrate (100 μl), followed by incubation at 20° to 25° C. for 20 minutes, and amplifier (200 μl), followed after a 10 minute incubation at 20° to 25° C. by a stopping solution (50 μl), and then reading the optical density of the solutions at 492 mm, as described in European Patent Application No. 84304328.

Prior to analysis the sample bearing swabs were divided into four groups and groups 2 and 4 were heated in aqueous extraction buffer at 80° C. for 15 minutes in a water bath.

Groups 1 and 2 were extracted with cold aqueous extraction buffer analysed as set out above using microtitre plates coated with antibody specific for Chlamydia trachomatis.

Groups 3 and 4 were analysed as set out above but on a microtitre plate coated with antibody not specific to Chlamydia trachomatis. The antibody was anti-prostatic acid phosphatase. The results are summarised in Table 1.

TABLE 1

| | | OD 492 mm | | | | | |
|---|---|---|---|---|---|---|---|
| | | UNHEATED | | | 80° FOR 15 MINUTES | | |
| Specimen Number | Culture | Chlamydia Antibody (1) | Non-Specific Antibody (3) | (1–3) | Chlamydia Antibody (2) | Non-Specific Antibody (4) | (2–4) |
| 1 | + | 2.73 | 2.77 | (0.04) | 1.11 | 0.14 | 0.97 |
| 2 | + | 2.73 | 2.43 | 0.30 | 2.76 | 0.18 | 2.58 |
| 3 | + | 2.74 | 2.78 | (0.04) | 0.74 | 0.26 | 0.48 |
| 4 | + | 1.71 | 0.17 | 1.54 | 0.20 | 0.19 | 0.01 |
| 5 | + | 2.76 | 2.62 | 0.14 | 0.98 | 0.23 | 0.75 |
| 6 | + | 2.62 | 2.66 | (0.04) | 0.25 | 0.28 | (0.03) |
| 7 | + | 0.19 | 0.18 | 0.01 | 0.23 | 0.30 | (0.07) |
| 8 | + | 0.18 | 0.16 | 0.02 | 0.15 | 0.29 | (0.14) |
| 9 | + | 0.20 | 0.15 | 0.05 | 0.38 | 0.35 | 0.03 |
| 10 | + | 0.19 | 0.19 | 0 | 0.17 | 0.32 | (0.15) |
| 11 | + | 0.21 | 0.21 | 0 | 2.78 | 0.21 | 2.57 |
| 12 | + | 0.48 | 0.36 | 0.12 | 0.21 | 0.40 | (0.19) |
| | sum | 16.74 | 14.68 | 2.06 | 9.96 | 3.15 | 6.81 |
| | mean | 1.395 | 1.22 | 0.17 | 0.83 | 0.26 | 0.56 |
| 13 | − | 2.79 | 2.79 | 0 | 0.17 | 0.15 | 0.02 |
| 14 | − | 2.85 | 2.84 | 0.01 | 0.17 | 0.16 | 0.01 |
| 15 | − | 2.76 | 2.84 | (0.08) | 0.17 | 0.18 | (0.01) |
| 16 | − | 2.78 | 2.70 | 0.08 | 0.16 | 0.18 | (0.02) |
| 17 | − | 2.86 | 2.79 | 0.07 | 0.16 | 0.16 | 0 |
| 18 | − | 0.21 | 0.18 | 0.03 | 0.16 | 0.16 | 0 |

TABLE 1-continued

| | | OD 492 mm | | | | | |
|---|---|---|---|---|---|---|---|
| | | UNHEATED | | | 80° FOR 15 MINUTES | | |
| Specimen Number | Culture | Chlamydia Antibody (1) | Non-Specific Antibody (3) | (1-3) | Chlamydia Antibody (2) | Non-Specific Antibody (4) | (2-4) |
| 19 | − | 1.28 | 1.29 | (0.01) | 0.16 | 0.16 | 0 |
| 20 | − | 2.62 | 2.67 | (0.05) | 0.18 | 0.18 | 0 |
| 21 | − | 0.22 | 0.23 | (0.01) | 0.20 | 0.17 | 0.03 |
| 22 | − | 2.67 | 2.59 | 0.08 | 0.18 | 0.24 | (0.06) |
| | sum | 21.04 | 20.92 | 0.12 | 1.71 | 1.74 | (0.03) |
| | mean | 2.10 | 2.09 | 0.01 | .17 | .17 | 0 |

Subtraction of the optical densities of Group 3 from Group 1 samples and of Group 4 from Group 2 samples gives a measure of the amount of non-specific binding encountered using unheated and heated sample swabs respectively.

The Data show that some non-heated positive samples bind almost equally well to non-specific antibody coated plates as to Chlamydia antibody coated plates. The Data show also that binding to non specific antibody coated plates by positive samples is generally reduced by heating samples at 80° C. In some cases binding to Chlamydia antibody coated plates by known positives is also reduced by heating indicating a measure of non-specific binding present in these samples. However binding by known negatives to either antibody is greatly reduced by heating allowing much greater accuracy in differentiating between positives and negatives using the assay.

EXAMPLE 2

Assays as described in Example 1 were carried out using Chlamydia specific plates after heating samples for varying times at 100° C. (boiling water bath). The results were as shown in Table 2.

TABLE 2

| | O.D. 492 nm | | | | | |
|---|---|---|---|---|---|---|
| | Unheated | 5 min | 10 min | 15 min | 40 min | |
| Positive Control | 0.48 | 0.75 | 1.23 | 1.68 | 1.49 | |
| Purified elementary bodies from chlamydia | 0.41 | 0.69 | 1.07 | 1.54 | 1.19 | |
| | | | | | | Reagent Blank |
| Swab Culture Positive | 0.22 | 0.24 | 0.29 | 0.39 | 0.38 | 0.15 |
| | 0.21 | 0.23 | 0.28 | 0.36 | 0.35 | 0.16 |
| | | | | | | Conjugate Blank |
| Swab Culture Negative Showing high non-specific binding | 0.74 | 0.50 | 0.23 | 0.21 | 0.18 | 0.23 |
| | 0.72 | 0.45 | 0.20 | 0.16 | 0.17 | 0.19 |

It can be seen that the signal from the positive control and culture positive specimen were optimised by 15 minutes heating and non-specific binding in the culture negative sample showing high non-specific binding was not detectable after 15 minutes boiling.

It can be seen from this example that heating does not only reduce the non-specific binding of negative samples, but can also enhance the signal given by positive specimens. This is especially valuable where small amounts of Chlamydia material is present in the specimen.

EXAMPLE 3

Samples were divided and treated as in Example 1 and analysed using specific and non-specific antibody plates, as in Example 1. The results appear in Table 3.

TABLE 3

| | | UNHEATED | | | 100° C. FOR 15 MINUTES | | |
|---|---|---|---|---|---|---|---|
| Specimen Number | Culture | Chlamydia Antibody (1) | Non-Specific Antibody (3) | (1-3) | Chlamydia Antibody (2) | Non-Specific Antibody (4) | (2-4) |
| 23 | + | 0.36 | 0.16 | 0.20 | 0.45 | 0.13 | 0.32 |
| 24 | + | 0.34 | 0.24 | 0.10 | 0.50 | 0.14 | 0.36 |
| 25 | + | 0.34 | 0.12 | 0.22 | 0.49 | 0.16 | 0.33 |
| 26 | + | 0.55 | 0.19 | 0.36 | 0.83 | 0.15 | 0.68 |
| 27 | + | 0.51 | 0.14 | 0.37 | 0.85 | 0.12 | 0.73 |
| 28 | + | 0.61 | 0.13 | 0.48 | 0.91 | 0.13 | 0.78 |
| | sum | 2.71 | 0.98 | 1.73 | 4.03 | 0.83 | 3.20 |
| | mean | 0.45 | 0.16 | 0.29 | 0.67 | 0.14 | 0.53 |
| 29 | − | 0.19 | 0.13 | 0.06 | 0.21 | 0.14 | 0.07 |
| 30 | − | 0.49 | 0.48 | 0.01 | 0.22 | 0.15 | 0.07 |
| 31 | − | 0.20 | 0.17 | 0.03 | 0.20 | 0.16 | 0.04 |
| 32 | − | 0.20 | 0.13 | 0.07 | 0.21 | 0.14 | 0.07 |
| 33 | − | 0.50 | 0.50 | 0 | 0.21 | 0.14 | 0.07 |
| 34 | − | 1.32 | 0.18 | 1.14 | 0.21 | 0.14 | 0.07 |
| 35 | − | 0.20 | 0.14 | 0.06 | 0.18 | 0.16 | 0.02 |
| 36 | − | 0.21 | 0.13 | 0.08 | 0.18 | 0.14 | 0.04 |
| 37 | − | 0.26 | 0.19 | 0.07 | 0.19 | 0.15 | 0.04 |

TABLE 3-continued

| Specimen Number | Culture | UNHEATED | | | 100° C. FOR 15 MINUTES | | |
|---|---|---|---|---|---|---|---|
| | | Chlamydia Antibody (1) | Non-Specific Antibody (3) | (1–3) | Chlamydia Antibody (2) | Non-Specific Antibody (4) | (2–4) |
| 38 | — | 0.35 | 0.26 | 0.09 | 0.19 | 0.13 | 0.06 |
| 40 | — | 0.21 | 0.18 | 0.03 | 0.20 | 0.13 | 0.07 |
| | sum | 4.34 | 2.66 | 1.68 | 2.40 | 1.71 | 0.69 |
| | mean | 0.36 | 0.22 | 0.14 | 0.20 | .14 | 0.06 |

In this case boiling significantly increased the signal from positive samples, i.e sensitivity was increased.

Boiling known culture-negative samples eliminated the occasional false positive signal, e.g. samples 34 and 38.

It can be seen from these Examples that heating the samples reduces non-specific binding and also may increase the amount of reaction product produced by the assay, making the assay more sensitive and increasing the effective "signal to noise ratio" obtained.

EXAMPLE 4

Effect of swab material on assay

Known positive samples in the form of swab materials of different types were extracted using cold and hot extraction buffer solutions of different make up.

The extraction solutions were as follows:
1. 100 mM triethanolamine
   0.1% w/v sodium azide
   0.1% v/v Triton X-705
   1.0 mM $MgCl_2$
   0.1 mM $ZnCl_2$
   pH 7.5
2. As 1, +1% w/v Byco A
3. As 2, without $ZnCl_2$ or $MgCl_2$
4. As 3, without Byco A "Byco A" is a hydrolysed gelatin.
   The swab materials used were:
   (a) Cotton wool
   (b) Sterilin albumin—coated swabs
   (c) "Westminster" polyester foam swabs.

100 μl. of a 1/100 dilution of a standard preparation of purified elementary bodies of C. trachomatis (strain L2), diluted in water, was loaded onto each of four swabs of each type, and onto each of four 160 mg. pledgets of the cotton wool.

Each loaded swab was immersed in 2 ml. of an extraction diluent, whirlimixed for approx 5 sec., and a 500 μl. aliquot removed as a "pre-boil" sample. The remaining fluids plus swabs were placed in a boiling waterbath for 15 min.

An assay as described in Example 1 for Chlamydia antigen was performed on the pre- and post-boil extracts.

RESULTS
(Absorbance at 492 nm)

| | Cotton Wool | | Albumin Coated | | Polyester Foam | |
|---|---|---|---|---|---|---|
| | Pre-boil | Post-boil | Pre-boil | Post-boil | Pre-boil | Post-boil |
| 1. | 0.524 | 1.288 | 0.247 | 0.807 | 0.404 | 1.070 |
| | 0.610 | 1.427 | 0.231 | 0.837 | 0.381 | 0.906 |
| 2. | 0.551 | 1.563 | 0.320 | 1.417 | 0.408 | 0.987 |
| | 0.600 | 1.508 | 0.343 | 1.462 | 0.417 | 1.140 |
| 3. | 0.666 | 0.745 | 0.188 | 0.327 | 0.419 | 0.445 |
| | 0.665 | 0.824 | 0.264 | 0.326 | 0.460 | 0.459 |
| 4. | 0.609 | 0.481 | 0.179 | 0.255 | 0.370 | 0.290 |
| | 0.669 | 0.478 | 0.175 | 0.236 | 0.266 | 0.287 |

It can be seen that the nature of the swab material affects the analysis, perhaps as a result of more or less antigen being extracted from the swab material because of binding of antigen to the swab material.

The nature of the eluent solution affects the assay result and the presence of zinc and/or magnesium ion is beneficial. To a lesser degree, the presence of hydrolysed gelatin is also shown to be beneficial.

Best results came from using cotton wool and the polyester foam swabs performed better than the albumin coated swabs.

EXAMPLE 5

Effect of $Zn^{2+}$ and $Mg^{2+}$ concentration of diluent solution

The following diluent solutions were used with and without heating to dilute known positive sample and the samples were then analysed generally as in Example 1.

The diluent solutions were as follows:
1. 100 mM triethanolamine
   0.1% w/v sodium azide
   0.1% v/v Triton X-705
   2.0% w/v Byco A
   pH 7.5
2. As 1, plus 0.5 mM $MgCl_2$, 0.05 mM $ZnCl_2$
3. As 1, plus 1.0 mM $MgCl_2$, 0.1 mM $ZnCl_2$
4. As 1, plus 2.0 mM $MgCl_2$, 0.2 mM $ZnCl_2$ The antigen was a lysate of McCoy cells infected with C. trachomatis, strain SA2F, diluted 1 in 10 in deionised water.

100 μl. of antigen was added to 2 ml. of each diluent, and "whirlmixed" for approx. 5 sec. A sample was reserved as "preboil" and the remainder was placed in a boiling waterbath for 15 min.

Duplicate 200 μl. aliquots of each fluid were assayed.

RESULTS
(Absorbance at 492 nm.)

| Diluent | Pre-boil | Post-boil |
|---|---|---|
| 1. | 0.494 | 0.474 |
| | 0.482 | 0.479 |
| 2. | 0.460 | 0.675 |
| | 0.477 | 0.645 |
| 3. | 0.541 | 0.846 |
| | 0.525 | 0.743 |
| 4. | 0.552 | 0.956 |

| RESULTS | | |
|---|---|---|
| (Absorbance at 492 nm.) | | |
| Diluent | Pre-boil | Post-boil |
| | 0.544 | 0.944 |

The combination of 2 mM $MgCl_2$ and 0.2 mM $ZnCl_2$ offers the best net result after boiling, i.e. increasing concentrations of $Mg^{2+}$ and $Zn^{2+}$ ion increase the sensitivity of the assay.

EXAMPLE 6

Effect of swab carrier material on assay

Swabs Used
1. Albumin coated cotton wool on wooden stick
2. Plain cotton wool on wooden stick
3. Plain cotton wood on plastic stick (All From Sterilin)

Antigen

100 μl. per swab of McCoy cell preparation of *C. trachomatis* strain SA2F, containing 1% formaldehyde, and diluted 1 in 50 in water.

Diluent
100 mM triethanolamine
0.1% v/v Triton X-705
0.1% w/v sodium azide
2 mM $MgCl_2$
0.2 mM $ZnCl_2$
2% w/v Byco A
0.5% w/v glucose pH 7.5

Procedure

Loaded swabs were placed in 2.0 ml. aliquots of diluent and left overnight. Similar controls containing the same amount of antigen but no swab were set up.

All samples were whirlimixed, 500 μl. aliquots were removed, and the remainder placed in a boiling waterbath for 15 minutes.

All fluids were then subjected to the assay procedure described in Example 1.

| RESULTS (Absorbance at 492 nm) | | | | | |
|---|---|---|---|---|---|
| 1 | | 2 | | 3 | |
| Pre-boil | Post-boil | Pre-boil | Post-boil | Pre-boil | Post-boil |
| 0.819 | 1.053 | 0.450 | 0.667 | 1.091 | 1.464 |
| 0.653 | 1.047 | 0.477 | 0.741 | 1.018 | 1.441 |
| 0.832 | 1.025 | 0.302 | 0.499 | 0.849 | 1.327 |
| 0.752 | 1.110 | 0.305 | 0.611 | 0.821 | 1.408 |
| 0.589 | 0.801 | 0.527 | 0.712 | 0.845 | 1.081 |
| 0.546 | 0.837 | 0.474 | 0.690 | 0.903 | 1.053 |
| 0.593 | 0.895 | 0.401 | 0.655 | 0.951 | 1.419 |
| 0.624 | 0.969 | 0.382 | 0.617 | 0.941 | 1.424 |
| 0.553 | 0.666 | 0.408 | 0.549 | 0.890 | 1.329 |
| 0.553 | 0.816 | 0.412 | 0.543 | 0.872 | 1.366 |
| 0.650 | 0.922 | 0.414 | 0.628 | 0.918 | 1.331 |
| control (no swab) | | 1.043 | 1.198 | | |
| | | 1.028 | 1.291 | | |

It may be seen that loss of antigen is less and recovery after boiling more when no wood is present in the swab.

EXAMPLE 7

Effect of heating Chlamydia antigen in Cell Culture Medium containing Foetal Calf Serum Sterilin swabs were loaded with formalinised Chlamydia antigen (1: 50 BCD $SA_2F$ in water), immersed in Eagles Minimum Essential Medium (Wellcome) containing 5% foetal calf serum, brought to pH 7.8 with sodium bicarbonate and left for 72 hours. No detergent was used.

An assay as described in Example 1 was performed on the fluids before and after heating on a boiling water bath for 15 minutes.

| RESULTS (Net Absorbance at 492 nm over controls) | | | | | |
|---|---|---|---|---|---|
| | Swab | | | | |
| | 1 | 2 | 3 | 4 | 5 |
| Pre-Boil | 0.405 | 0.645 | 0.347 | 0.648 | 0.442 |
| | 0.442 | 0.557 | 0.338 | 0.659 | 0.378 |
| Post Boil | 1.758 | 1.537 | 1.514 | 1.875 | 1.387 |
| | 1.688 | 1.552 | 1.560 | 1.695 | 1.462 |

It is clearly shown that boiling in Eagles MEM+5% calf serum enhances the signal obtained from Chlamydia antigen in the assay.

I claim:

1. A process for determining qualitatively or quantitatively the presence of *Chlamydia trachomatis* or *Chlamydia trachomatis* derived material in a subject material comprising the steps of
   (i) deriving a sample from said subject material containing *Chlamydia trachomatis* derived lipopolysaccharide material,
   (ii) contacting said sample with a first antibody bound to a solid surface, wherein the first antibody is specific for *Chlamydia trachomatis* derived material, thereby to bind at least a portion of the *Chlamydia trachomatis* derived lipopolysaccharide material to the surface by means of the first antibody,
   (iii) contacting the bound *Chlamydia trachomatis* derived lipopolysaccharide material with a conjugate between a second antibody, which is the same or different from the first antibody and is capable of binding selectively to the *Chlamydia trachomatis* derived lipopolysaccharide material and an enzyme system so that said conjugate binds to said bound *Chlamydia trachomatis* derived lipopolysaccharide material,
   (iv) carrying out a reaction catalyzed by said enzyme, and
   (v) determining a product of said reaction, wherein the sample is derived from the subject material by a process which comprises heating the subject material to a temperature of from 70° to 110° C. for at least 5 minutes.

2. A process as claimed in claim 1 wherein the material is heated to a temperature of from 80° to 100° C.

3. A process as claimed in claim 1 wherein the material is maintained at the elevated temperature for from 5 to 30 minutes.

4. A process as claimed in claim 3 wherein the material is maintained at the elevated temperature for approximately 15 minutes.

5. A process as claimed in claim 1 wherein the conjugated enzyme is a phosphatase.

6. A process as claimed in claim 1 wherein the reaction system catalyst catalyses a first reaction which produces a modulator for a secondary part of the reaction system.

7. A process as claimed in claim 5 wherein the conjugated phosphatase is employed to convert NADP to NAD and the NAD is employed as a modulator for a reduction/oxidation reaction through an NAD/NADH cycle.

8. A process for determining qualitatively or quantitatively the presence of *Chlamydia trachomatis* or *Chlamydia trachomatis* derived material in a subject material comprising the steps of
  (i) deriving a sample from said subject material containing *Chlamydia trachomatis* derived lipopolysaccharide material,
  (ii) contacting said sample with an antibody for a *Chlamydia trachomatis* derived lipopolysaccharide material bound to a solid surface so that at least a portion of the *Chlamydia trachomatis* derived lipopolysaccharide material is bound,
  (iii) contacting the bound *Chlamydia trachomatis* lipopolysaccharide material with a conjugate between a substance capable of binding selectively to the *Chlamydia trachomatis* derived lipopolysaccharide material and a catalyst for a reaction system so that said conjugate binds to said bound *Chlamydia trachomatis* derived lipopolysaccharide material,
  (iv) carrying out the reaction system catalyzed by said catalyst, and
  (v) determining a product of said reaction system,
wherein the sample is derived from the subject material by a process which comprises boiling the sample derived from the subject material for a period of time to enhance the determination prior to carrying out the determination.

9. A process as claimed in claim 8 wherein the sample derived from the subject material is boiled for a period from 5 to 30 minutes.

10. In a process for determining qualitatively or quantitatively the presence of *Chlamydia trachomatis* or *Chlamydia trachomatis* derived material in a subject material which process comprises deriving a sample from said subject material containing *Chlamydia trachomatis* derived lipopolysaccharide material, contacting the *Chlamydia trachomatis* derived lipopolysaccharide material with a support which will bind the *Chlamydia trachomatis* derived lipopolysaccharide material, washing the support to leave the *Chlamydia trachomatis* derived lipopolysaccharide material bound to the support, contacting the bound *Chlamydia trachomatis* derived lipopolysaccharide with a conjugate between an antibody which will bind selectively to the *Chlamydia trachomatis* derived lipopolysaccharide material and an enzyme, thereby to bind said conjugate to said bound *Chlamydia trachomatis* derived lipopolysaccharide material, carrying out a reaction catalysed by said enzyme and determining a product of said reaction, the improvement comprising boiling the sample derived from the subject material for a period of time to enhance the determination prior to carrying out the determination.

* * * * *